United States Patent [19]

Dewald et al.

[11] Patent Number: 4,701,456
[45] Date of Patent: Oct. 20, 1987

[54] AMINOALKOXYBENZOPYRANONES AS ANTIPSYCHOTIC AND ANXIOLYTIC AGENTS

[75] Inventors: Horace A. Dewald; Lawrence D. Wise; Thomas G. Heffner, all of Ann Arbor, Mich.

[73] Assignee: Warner-Lambert Company, Morris Plains, N.J.

[21] Appl. No.: 745,971

[22] Filed: Jun. 18, 1985

Related U.S. Application Data

[63] Continuation-in-part of Ser. No. 651,972, Sep. 19, 1984, abandoned.

[51] Int. Cl.$^4$ .................. A61K 31/505; C07D 405/14
[52] U.S. Cl. ...................... 514/253; 514/256; 514/269; 514/318; 514/320; 514/337; 544/295; 544/298; 544/333; 544/357; 544/364; 544/376; 544/405; 546/194; 546/196; 546/256; 546/269
[58] Field of Search .............. 544/295, 298, 333, 405, 544/364, 357, 376; 514/253, 256, 269, 337, 318, 320; 546/194, 196, 269, 256

[56] References Cited

U.S. PATENT DOCUMENTS

| | | | |
|---|---|---|---|
| 3,810,898 | 5/1974 | Witte et al. | 514/870 |
| 3,959,283 | 5/1976 | Lafon | 544/295 |
| 4,405,622 | 9/1983 | Kluge | 544/295 |
| 4,539,207 | 9/1985 | Brown | 544/405 |

Primary Examiner—Glennon H. Hollrah
Assistant Examiner—James H. Turnipseed
Attorney, Agent, or Firm—Joan Thierstein

[57] ABSTRACT

Aminoalkyoxybenzopyranones of the formula

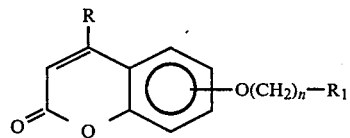

wherein $R_1$ is of the formula

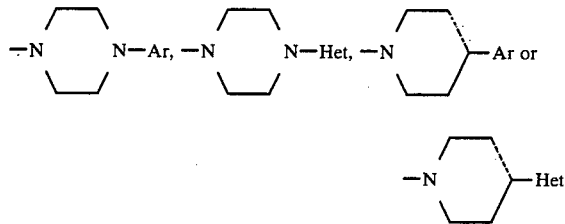

are described as well as methods of preparation, pharmaceutical compositions and methods for treating anxiety and psychoses such as schizophrenia therewith.

16 Claims, No Drawings

AMINOALKOXYBENZOPYRANONES AS ANTIPSYCHOTIC AND ANXIOLYTIC AGENTS

This application is a continuation-in-part of U.S. Ser. No. 651,972 filed Sept. 19, 1984, now abandoned.

BACKGROUND OF THE INVENTION

Various aminoalkoxybenzopyranones have been described in the literature. Compounds of the formula:

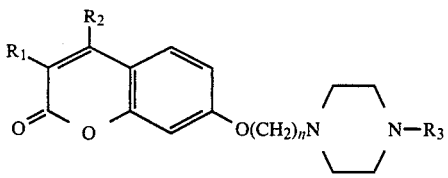

wherein $R_2$ is lower alkyl have been described in U.S. Pat. No. 3,810,898 as having antioedematous activity and the ability to reduce increased capillary permeability.

The present benzopyranones have been found to have valuable neuroleptic properties and as such are useful as antipsychotic agents and as anxiolytic agents.

SUMMARY OF THE INVENTION

Accordingly, the present invention relates to a compound of the formula

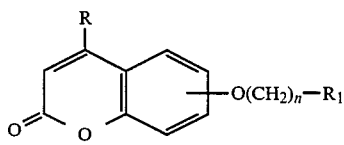

I wherein n is an integer from 2–5; R is hydrogen, lower alkyl, trifluoromethyl, or lower alkoxy; $R_1$ is a radical of the formula

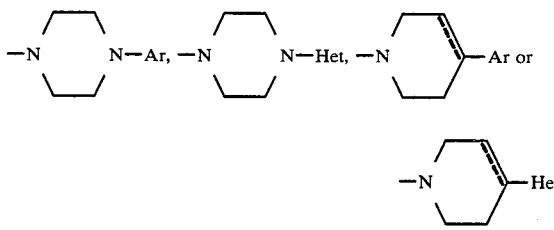

in which ---- represents a single or double bond, Ar is phenyl or phenyl substituted by lower alkyl, lower alkoxy, lower thioalkoxy, halogen, or trifluoromethyl, and Het is 2-, 3- or 4-pyridinyl or 2-, 3- or 4-pyridinyl substituted by lower alkyl, lower alkoxy, or halogen; 2-, 4-, or 5-pyrimidinyl or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl or 2- or 3-thienyl substituted by lower alkyl or halogen, 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid addition salt thereof, with the exclusion of the compound wherein n is 3, R is methyl, and $R_1$ is a radical of the formula

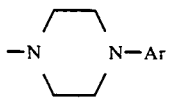

in which Ar is phenyl.

The present invention also relates to a pharmaceutical composition comprising an antipsychotic effective amount or an anxiolytically effective amount of a compound of Formula I as a pharmaceutically acceptable acid addition salt thereof with a pharmaceutically acceptable carrier.

The present invention further relates to a method of treating psychoses, e.g., schizophrenia, or to a method of treating anxiety, in a subject suffering therefrom comprising administering to said subject an effective amount of a compound of the Formula I, wherein n is an integer from 2–5; R is hydrogen, lower alkyl, lower alkoxy, or trifluoromethyl; $R_1$ is a radical of the formula

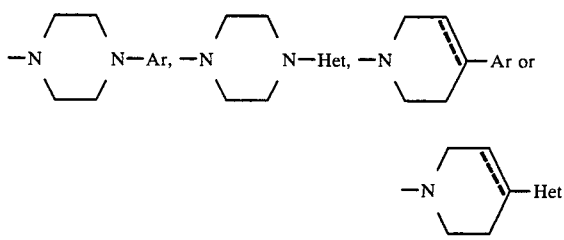

in which ---- represents a single or double bond, Ar is phenyl or phenyl substituted by lower alkyl, lower alkoxy, lower thioalkoxy, halogen, or trifluoromethyl, and Het is 2-, 3-, or 4-pyridinyl or 2-, 3-, or 4-pyridinyl substituted by lower alkyl, lower alkoxy, or halogen, 2-, 4-, or 5-pyrimidinyl, or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl, or 2- or 3-thienyl substituted by lower alkyl or halogen, 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid addition salt thereof in unit dosage form.

DETAILED DESCRIPTION

In the compounds of the Formula I, the term "lower alkyl" is meant to include a straight or branched alkyl group having from one to six carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine, or bromine.

Lower alkoxy and thioalkoxy are O-alkyl or S-alkyl of from one to six carbon atoms as defined above for "lower alkyl."

A preferred embodiment of the present invention is a compound of the Formula II

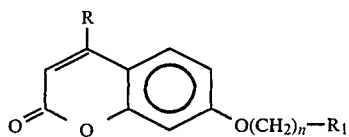

wherein n, R, and $R_1$ are as defined above, or a pharmaceutically acceptable acid addition salt thereof.

Another preferred embodiment of the present invention is a compound of the Formula II, wherein n is an integer of 2–5; R is hydrogen, and $R_1$ is as defined previously, or a pharmaceutically acceptable acid addition salt thereof.

Another preferred embodiment is a compound of the Formula II, wherein n is 2–5; R is hydrogen, and $R_1$ is a radical of the formula

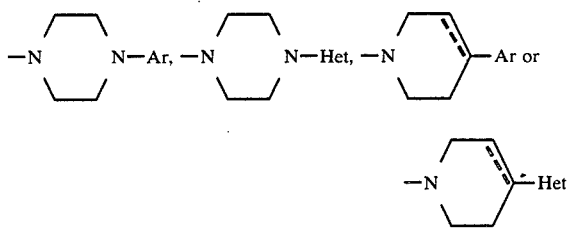

in which ⁼⁼⁼ is a single or double bond; Ar is phenyl or phenyl substituted by methyl, methoxy, thiomethoxy, or chloro, and Het is 2-, 3-, or 4-pyridinyl; 2-, 3-, or 4-pyridinyl substituted by methyl, chloro, or bromo; 2-, 4- or 5-pyrimidinyl; 2-pyrazinyl, or 2-thiazolyl.

Still another preferred embodiment is a compound of the Formula II, wherein n is 2–5, but more preferably 3 or 4; R is hydrogen, and $R_1$ is a radical of the formula

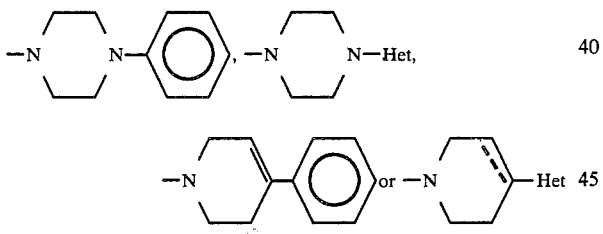

in which Het is 2-, 3-, or 4-pyridinyl; 2-, 4-, or 5-pyrimidinyl; 2-pyrazinyl or 2-thiazolyl.

Particularly preferred embodiments of the present invention are; 7-[3-(4-phenyl-1-piperazinyl)propoxy]-2H1-benzopyran-2-one, 7-[3-(1,2,3,6-tetrahydro-4-phenyl-1-pyridinyl)propoxy]-2H-1-benzopyran-2-one, 7-[3-[4-(2-pyrimidinyl)-1-piperazinyl]propoxy]-2H-1-benzopyran-2-one, and 7-[4-phenyl-1-piperazinyl)-butoxy]-2H-1-benzopyran-2-one, or a pharmaceutically acceptable acid addition salt thereof.

In addition to the previous preferred compounds, a particular preferred embodiment of the method for treating psychoses aspect of the invention comprises treating a host with an effective amount of 7-[3-(4-phenyl-1-piperazinyl)-propoxy]-4-methyl-2H-1-benzopyran-2-one in unit dosage form.

The compounds of the invention form pharmaceutically acceptable acid addition salts with organic and inorganic acids. Examples of suitable acids for salt formulation are hydrochloric, sulfuric, phosphoric, acetic, citric, oxalic, malonic, salicylic, malic, fumaric, succinic, ascorbic, maleic, methanesulfonic, and the like. The salts are prepared by contacting the free base form with a sufficient amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The compounds of the present invention and of the Formula I may be prepared by first reacting a hydroxy-2H-1-benzopyran-2-one of the formula

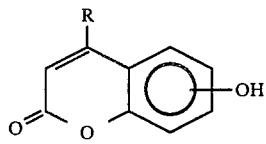

wherein R is as defined previously, with a compound of the formula

wherein n is an integer of 2–5; X and Y are the same or different and are a leaving group such as halogen or a sulfonyloxy group, for example, methanesulfonyloxy or p-toluenesulfonyloxy; and secondly, reacting the resulting product of the Formula IV

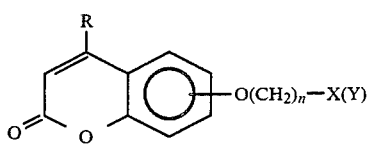

with an amine selected from the formula

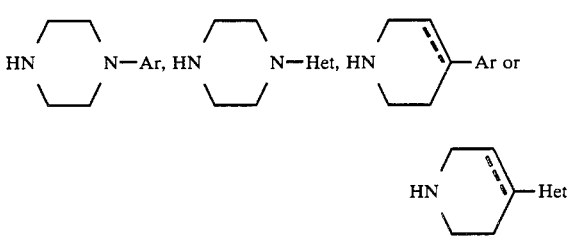

wherein Ar and Het are as defined previously, and, if desired, converting the resulting free base by known methods to a pharmaceutically acceptable acid addition salt.

The reaction of the benzopyran-2-one of Formula III with a compound of Formula IIIa is carried out in an inert solvent, preferably a polar solvent such as a ketone, for example, acetone or methyl isobutyl ketone, in the presence of an acid scavenger, such as, for example, sodium or preferably, potassium carbonate in anhydrous form, at the reflux temperature of the solvent.

The intermediate product of Formula IV is then reacted with the appropriate amine in a polar aprotic solvent such as, for example, dimethylformamide and in the presence of a neutralizing agent such as, for example, sodium bicarbonate. The reaction is carried out at elevated temperatures, e.g., from about 50° to 150° C.

An alternate method for the preparation of a compound of Formula I is to first prepare a compound of the formula $$X(CH_2)_nR_1 \qquad V$$

wherein $R_1$ and X are as defined above, according to a method described in Ind. J. Chem. 435 (1982), and react said compound of Formula V directly with a benzopyran-2-one of Formula III. This reaction is also best carried out at elevated temperatures, e.g., 50°–150° C., in a solvent such as dimethylformamide and in the presence of an acid neutralizing agent such as sodium bicarbonate.

The appropriate hydroxy-coumarin derivatives, compounds of Formula III, and amine derivatives are available commercially or may be prepared by well-known methods. For example, 4-substituted-7-hydroxy-coumarins are prepared by slight variations on the method described in Organic Synthesis, Coll Vol 3, p 282, for preparing 4-methyl-7-hydroxy-coumarin.

The compounds of the present invention are new chemical substances which are useful as pharmaceutical agents for the treatment of psychoses such as, for example, schizophrenia. The antipsychotic activity of representative compounds of the invention was established by the Mouse Activity and Screen Test Procedure (MAST) described below:

ANIMALS: Nine unfasted Swiss-Webster male mice (Buckberg Labs) weighing 20-30 g are equally divided into three groups for each drug dose to be tested. That is, data for each dose level was generated by three separate groups of three mice each.

DRUGS: A minimum of three dose levels (10, 30, and 100 mg/kg) are tested for each drug. Treatments are administered intraperitoneally one hour prior to testing. All dosages are calculated as parent compound and given in volumes of 10 mg/kg. Compounds are dissolved or suspended in 0.2% Methocel. Control animals are injected with Methocel.

TESTING: A two-part testing procedure is started one hour postinjection. First, the screen test is performed (see Pharmac Biochem Behav 6, 351-353, 1977). Briefly, this test consists of placing mice on individual wire screens which are then rotated 180° at the start of a 60-second observation period. The number of mice falling off the inverted screen is recorded.

Immediately following the screen test, the final phase of testing is initiated by placing each group of three mice in one actophotometer (Life Sciences, 22, 1067-1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten-minute intervals for 60 minutes.

DATA: The data obtained from the screen test are expressed as percent of mice falling off the screen. Data derived from locomotor activity of drug-treated mice are compared to the activity of vehicle-treated animals and are expressed as percent inhibition of spontaneous locomotion. All percentages reported for inhibition of locomotion are based upon data accumulated for one hour. Both phases of testing are graded: A=60-100%; C=31-59%; and N=0-30%. An overall dose rating is obtained by the following criteria.

| Inhibition of Locomotion rating | with | Screen Test Failure Rating | = | Dose Rating |
|---|---|---|---|---|
| A | — | N or C | = | A |
| A | — | A | = | C |
| C | — | N or C | = | C |
|  |  | All other combinations | = | N |

Compounds which exhibit an overall dose rating of A at a dose of 100 milligrams/kilogram or less are considered active. Utilizing this procedure, an overall dose rating of A was obtained for the noted compounds at the indicated dose as reported in Table 1.

TABLE 1

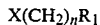

| R | n | $R_1$ | Dose mg/kg |
|---|---|---|---|
| H | 3 | —N(piperazinyl)—phenyl | 3.0 |
| $CH_3$ | 3 | —N(piperazinyl)—phenyl | 1.0 |
| H | 3 | —N(piperazinyl)—pyrimidinyl | 3.0 |
| H | 3 | —N-(4-phenylpiperidinyl) | 1.0 |
| Thioridazine | | | 10.0 |

The antipsychotic activity of representative compounds of the invention was also established by the [³H] haloperidol binding assay method (HRBA) which is described in Mol. Pharmacol. 12, 800 (1976) and reports excellent correlation between the amount of binding and clinical potency.

[³H] Haloperidol Binding Assay. The relative affinities of compounds for dopamine receptors were evaluated on the basis of their ability to displace [³H] haloperidol from striatal membranes prepared from Long-Evans hooded rats. Rats were decapitated; the brains were removed, and the corpus striata were dissected. The corpus striata were homogenized in 40 volumes of 50 nM Tris buffer (pH 7.6) and centrifuged. Pellets were rehomogenized in 50 volumes of the same buffer and used for the binding assay. Incubations were carried out in 10 ml of 50 nM Tris-HCl buffer (pH 7.6) containing 2 mg/ml of original wet tissue weight of homogenate, 100 μl of test agent or solvent, and 0.6 nM of [$^3$H] haloperidol. Nonspecific binding was determined in the presence of 0.1 μM (+)-butaclamol. Samples were incubated in reciprocating water bath at 25° C. for 40 minutes. Incubation was terminated by rapid filtration under reduced pressure through glass fiber filters (Whatman GF/B). The filters were rinsed three times with 10 ml of Tris-HCl buffer. The filters were placed in 10 ml of scintillation coctail (Beckman Ready-Solv HP) and shaken for one hour. Radioactivity retained on the filter was determined by liquid scintillation spectrophotometry. Compounds were initially evaluated at 10 nM. $IC_{50}$s when determined were calculated from a nonlinear computer curve, fit on the data from four or more concentrations, each done in triplicate.

$IC_{50}$s for representative compounds of the present invention are reported in Table 2.

TABLE 2

HRBA Assay

[Structure: R on 4-position of 2H-benzopyran-2-one with O(CH$_2$)$_n$R$_1$ at 7-position]

| R | n | R$_1$ | $IC_{50}$ |
|---|---|---|---|
| H | 3 | —N(piperazinyl)—phenyl | $1.5 \times 10^{-8}$ |
| CH$_3$ | 3 | —N(piperazinyl)—phenyl | $5. \times 10^{-8}$ |
| H | 3 | —N(piperazinyl)—pyrimidinyl | $93 \times 10^{-8}$ |
| H | 3 | —N(tetrahydropyridinyl)—phenyl | $1.6 \times 10^{-8}$ |
| Thioridazine | | | $1.9 \times 10^{-9}$ |

The compounds of the present invention are new chemical substances which are also useful as pharmaceutical agents for the treatment of anxiety, i.e., anxiolytic agents. The antianxiety activity of a representative compound showing such activity for the compounds of the Formula I of the present invention is established by the use of an animal model of anxiety based on the Geller-Seifter conflict test described in Psychopharmacologia 1:482 (1960). Particularly the test follows initial shaping of response, an experimental conflict is induced, with animals trained until stable performance is established. Each animal serves as his own control. A description of the test is as follows:

Subjects: Mature male hooded rats (Long-Evans strain) 300–350 g body weight.

Apparatus: The experimental chamber consists of an inner test compartment with a lever mounted in one wall, a grid floor, an automatic feeding device, and a speaker. This chamber is enclosed by a sound insulated cubicle. Shock is provided by a LVE Model 1531 Constant Current SHocker. White (masking) noise is supplied by a LVE Model 1524 Noise Generator. A tone is produced by a LVE Model 1664 4.5 KC Tone Generator. All events and recordings are automatic and are programmed with appropriate electric timers and relay devices.

Procedure: Variable interval (VI)=two-minute; trial periods=four; shock=0.6 to 0.8 ma; food reward-=Borden's Sweetened Condensed Milk diluted two parts water to one part milk; animals are deprived to 70% of their free feeding weight and are 23 hours starved; session length=one hour and 12 minutes.

The conflict is induced in the following manner: hungry rats are conditioned to press a lever to obtain a food reward. Reinforcement is contingent upon a lever press and occurs at variable intervals on the average of once every two minutes—VI two-minute (See Ferster; C. B., and Skinner, B. F., "*In Schedules of Reinforcement,*" Appleton-Century-Crofts, New York, 1957).

Spaced at regular intervals throughout the experimental session are four three-minute periods. During these trial periods a tone signals that every lever press will be food reinforced (CRF) and simultaneously punished by a painful electric foot shock.

In other words, food-deprived rats are trained to depress a lever in order to obtain food (sweetened condensed milk). Normally, the rats perform on a variable interval (VI) schedule on which a lever press results in food delivery on the average of once every two minutes; the time between successive periods of food availability is varied continuously such that animals respond at low but steady rates to obtain occasional access to food. After animals perform for 12 minutes on this schedule the house lights are extinguished and two small stimulus lights are illuminated, signaling the availability of food for each depression of the lever during a three minute trial period. During the trial, each depression of the lever also results in the delivery of mild electric shock (0.8 ma, 0.25 second duration) delivered through the grid floor (punishment). Thus, an approach-avoidance conflict is established with associated anxiety: food is readily available for each response, but each respone is punished (see Miller, N. E., "Some Recent Studies of Conflict Behavior and Drugs," Am. Pharmacologist, 16: 12, 1961). The scheduled used in our test employed four successive trials, each preceded by a 12-minute period during which the food-reinforced VI was in effect.

During sessions in which no drug is administered, rats normally respond at steady rates on the VI component but emit very few responses during the punished trial period.

7-[3-[4-(2-pyrimidinyl)-1-piperazinyl]propoxy]-2H-benzopyran-2-one increased responding during trial periods at doses to the rat of 55 and 80 mg/kg PO, but not at 27.5 mg/kg PO. This effect was selective in that it was not accompanied by decreased responding during the VI component. In other words, there is a notable absence of gross sedation. This compound produced increases in punished responding in three of four rats tested with 55 mg/g and in four of four rats tested with 80 mg/kg. The total number of punished responses made by the four subjects in the pretest and test sessions for the noted compound are as follows.

| Compound | Dose (mg/ kg PO) | Total Punished Pretest | Responses Test |
| --- | --- | --- | --- |
| 7-[3-[4-(2-pyrimidinyl)-1-piperazinyl]propoxy]-2H—benzopyran-2-one | 27.5 | 39 | 44 |
| | 55 | 78 | 147 |
| | 80 | 23 | 77 |

The pretest responses are cummulative responses emitted during the three minute tests from a previous nondrug session.

An increase in responses during the trial periods (attenuation of conflict) indicates minor tranquilizer activity. This is shown by an increase in the trial/pretrial ratio. Total response rate is a measure of debilitating side effects. A decrease in total responses indicates side effect.

The compounds of the present invention can be prepared and administered in a wide variety of oral and parenteral dosage forms. It will be obvious to those skilled in the art that the following dosage forms may comprise as the active component, either a compound of Formula I, a corresponding pharmaceutically acceptable salt of a compound of Formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low-melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liguid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 0.1 mg to about 10 mg per kilogram daily. A daily dose range of about 1.0 mg to about 10 mg per kilogram is preferred.

In therapeutic use as anxiolytic agents, the compounds utilized in the pharmaceutical method of this invention are administered at the initial dosage of about 0.1 mg/kg to about 20 mg/kg daily. A daily dose range of about 1 mg/kg to about 3 mg/kg is preferred.

The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

7-[3-(4-Phenyl-1-piperazinyl)propoxy]-2H-1-benzoypyran-2-one 7-(3-halopropyloxy)-2H-1-benzopyran-2-one A mixture of 32 g (0.3 mol) of 7-hydroxy-2H-1-benzopyran-2-one, 43 g (0.3 mol) anhydrous potassium carbonate, and 48 g (0.3 mol) of 1-bromo-3-chloropropane in 350 ml of acetone is stirred under reflux for 18 hours. The mixture is filtered, and the filtrate is evaporated in vacuo. The residue is dissolved in dichloromethane and washed with water. The organic phase is dried over anhydrous magnesium sulfate and evaporated in vacuo. The remaining crude product is recrystallized from ethyl acetate-petroleum ether. There is obtained 32 g (68%) of solid, mp. 92°-98° C., which is a mixture of 7-(3-chloropropoxy)- and 7-(3-bromopropoxy)-2H-1-benzopyran-2-one.

7-[3-(4-Phenyl-1-piperazinyl)propoxy]-2H-1-benzopyran-2-one

A mixture of 6.3 g (0.025 mol) of 7-(3-halopropoxy)-2H-1-benzopyran-2-one, 10 g (0.12 mol) sodium bicarbonate, and 4.1 g (0.025 mol) of 1-phenylpiperazine in 100 ml of dimethylformamide is stirred and heated at 80° C. for 16 hours. The mixture is filtered, and the filtrate is evaporated in vacuo. The residue is dissolved in dichloromethane and extracted with water. The organic phase is dried over anhydrous magnesium sulfate and evaporated in vacuo. The residue is crystallized from ethyl acetate to give 5.9 g (61%) of title compound, mp. 117°–118° C.

EXAMPLE 2

7-[3-[4-(2,3-Dimethylphenyl)-1-piperazinyl]propoxy]-2H-1-benzopyran-2-one

By the same procedure as in Example 1 but using 4.8 g (0.025 mol) of 1-(2,3-dimethylphenyl)piperazine in place of 1-phenylpiperazine, there is obtained 3.7 g (37%) of title compound, mp. 89° C., from ethyl acetate. The corresponding hydrochloride salt was obtained by dissolving the free base in 10% isopropanolic hydrogen chloride and dilution with ethyl acetate, mp. 247°–250° C.

EXAMPLE 3

In an analagous manner as in Example 1, the following compounds were prepared:

7-[3-(4-phenyl-1-piperazinyl)-propoxy]-4-methyl-2H-1-benzopyran-2-one, m.p. 127°–130° C., its hydrochloride, m.p. 253° C.;

7-[3-[4-(2,3-dimethylphenyl)-1-piperazinyl]propoxy]-4-methyl-2H-1-benzopyran-2-one hydrochloride, m.p. 253°–255° C.;

7-[3-[4-(2-methylphenyl)-1-piperazinyl]propoxy]-2H-benzopyran-2-one, m.p 123°–125° C.;

7-[4-(4-phenyl-1-piperazinyl)butoxy]-2H-1-benzopyran-2-one, m.p. 145°–147° C.;

7-[3-(4-phenyl-1-piperazinyl)propoxy]-4-trifluoromethyl-2H-1-benzopyran-2-one, dihydrochloride, m.p. 190° C.;

7-[3-[4-(3-methylphenyl-1-piperazinyl]propoxy]-2H-1-benzopyran-2-one hydrochloride, m.p. 217°–220° C.;

7-[3-[4-(4-methylphenyl)-1-piperazinyl]propoxy]-2H-1-benzopyran-2-one, m.p. 140° ∝ 142° C.;

7-[3-[4-(3-chlorophenyl)-1-piperazinyl]propoxy]-2H-1-benzopyran-2-one hydrochloride, m.p. 228° C.;

7-[3-[4-(4-chlorophenyl)-1-piperazinyl]propoxy]-2H-1-benzopyran-2-one, m.p. 129°–131° C.;

7-[3-[4-(2,3-dichlorophenyl)-1-piperazinyl]-proxy]-2H-1-benzopyran-2-one hydrochloride, m.p. 215° C.

7-[3-[4-(3,4-dimethylphenyl)-1-piperazinyl]propoxy]-2H-1-benzopyran-2-one, m.p. 132° C., its hydochloride, m.p. 220° C.;

7-[3-[4-(3,4-dichlorophenyl)-1-piperazinyl]propoxy]-2H-1benzopyran-2-one, m.p. 135°–136° C.;

8-[3-(4-phenyl-1-piperazinyl)propoxy]-2H-1-benzopyran-2-one, m.p. 95°–97° C.;

7-[3-[4-(2-pyrimidinyl)-1-piperazinyl]propoxy]-2H-1-benzopyran-2-one, m.p. 135°–137° C.;

7-[3-[4-(3-chloro-2-pyridinyl)-1-piperazinyl]propoxy]-2H-1-benzopyran-2-one hydrochloride, m.p. 235°–238° C.;

7-[3-[4-(3-pyridinyl)-1-piperazinyl]propoxy]-2H-1-benzopyran-2-one, m.p. 122°–125° C.;

7-[3-[4-(6-fluoro-2-pyridinyl)-1-piperazinyl]propoxy]-2H-1-benzopyran-2-one hydrochloride, m.p. 241°–243° C.;

7-[3-[4-(6-bromo-2-pyridinyl)-1-piperazinyl]propoxy]-2H-1-benzopyran-2-one, m.p. 95°–97° C.;

7-[3-[4-(5-methyl-2-pyridinyl)-1-piperazinyl]propoxy]-2H-1benzopyran-2-one, m.p. 120°–122° C.;

7-[3-[4-(3-methyl-2-pyridinyl)-1-piperazinyl]propoxy]-2H-1-benzopyran-2-one hydrochloride, m.p. 210°–215° C.;

7-[3-[4-(4-methyl-2-pyridinyl)-1-piperazinyl]propoxy]-2H-1-benzopyran-2-one, m.p. 113°–115° C.;

7-[3-[4(6-methyl-2-pyridinyl)-1-piperazinyl]propoxy]-2H-1-benzopyran-2-one, m.p. 105°–107° C.;

7-[3-(1,2,3,6-tetrahydro-4-phenyl-1-pyridinyl)propoxy]-2H-1-benzopyran-2-one, m.p. 127° C.;

7-[2-(1,2,3,6-tetrahydro-4-phenyl-1-pyridinyl)ethoxy]-2H-1-benzopyran-2-one, m.p. 120°–125° C.;

7-[4-(1,2,3,6-tetrahydro-4-phenyl-1-pyridinyl)butoxy]-2H-1-benzopyran-2-one hydrochloride, m.p. 195° C.; and 7-[3-(1,2,3,6-tetrahydro-4-phenyl-1-pyridinyl)propoxy]-4-methyl-2H-1-benzopyran-2-one hydrochloride, m.p. 219°–221° C.;

7-[3-[4-(2-methylthiophenyl)-1-piperazinyl]propoxy]-2H-benzopyran-2-one hydrochloride, m.p. 228°–232° C.;

7-[3-[4-(2-methoxyphenyl)-1-piperazinyl]propoxy]-2H-benzopyran-2-one hydrochloride, m.p. 228°–231° C.;

7-[3-(1,2,3,4,5,6-hexahydro-4-phenyl-1-pyridinyl]propoxy]-2H-1-benzopyran-2-one hydrochloride, m.p. 218°–221° C.;

7-[3-[4-(2-pyrazinyl)-1-piperazinyl]propoxy]-2H-1-benzopyran-2-one, m.p. 176°–179° C.; and 7-[3-[4-(2-thiazolyl)-1-piperazinyl]propoxy]-2H-1-benzopyran-2-one hydrochloride, m.p. 167°–170° C.

EXAMPLE 4

7-[3-(4-Phenyl-1-piperazinyl)propoxy]-4-propyl-2H-1-benzopyran-2-one $N^1$-(3-chloropropoxy)$N^4$-phenylpiperazine was prepared as described in Ind. J. Chem. 435 (1982) by adding dropwise 87 g (0.55 mole) of 1-bromo-3-chloropropane to a stirred solution of 81 g (0.5 mole) of N-phenylpiperazine in 100 ml acetone and 75 ml of 25% aqueous sodium hydroxide. The organic layer was separated, concentrated, slurried with ethyl acetate, washed, dried over magnesium sulfate, and concentrated to an oil weighing 85 g and analyzed by thin layer chromatography and mass spectrometry to be the title compound.

The above compound as an oil, 4.6 g (0.02 mole), was reacted with 4.4 g (0.02 mole) of 7-hydroxy-4-propyl coumarin in 100 ml of dimethylformamide and 4 g of anhydrous potassium carbonate. The reaction mixture was stirred at 85°–95° C. for 16 hours. The mixture was filtered, concentrated, and the oil taken up in methylene chloride which solution was washed with sodium bicarbonate, dried over anhydrous magnesium sulfate, and concentrated. The oil solidified on standing and is recrystallized from ethyl acetate to afford 5 g of 7-[3-(4-phenyl-1-piperazinyl)propoxyl]-4-propyl-2H-1-benzopyran-2-one, m.p. 114°–116° C.

EXAMPLE 5

7-[3-[3,6-dihydro-4-(2-thienyl)-1(2H)-pyridinyl]propoxy]-2H-1-benzopyran-2-one, 4-(2-thienyl)tetrahydropyridine A solution under nitrogen of 1.3 g (0.01 mole) AlCl$_3$ in 40 ml ether is aded to a stirred suspension of 1.2 g (0.03 mole) LAH in 100 ml ether and 75 ml tetrahydrofuran at 15° C., then stirred for 15 minutes. To the stirred suspension is added slowly a solution of 3 g (0.018 mole) 4-(2-(thienyl)-pyridine on 30 ml of tetrahydrofuran. The mixture is stirred at room temperature for about five hours, then decomposed by cautious addition of 2 ml H₂O, 3 ml 40% NaOH, 2 ml H₂O. The mixture is filtered, and evaporated in vacuo. The residue is partitioned in 1N HCl-ether. The aqueous portion is mixed with methylene dichloride and made basic with concentrated NaOH. The methylene dichloride layer is dried (MgSO₄) and evaporated in vacuo to obtain 2 g of 4-(2-thienyl)tetrahydropyridine.

Mass spec. calcd. 165.25, Found: 165.

A 2.9 g (0.012 mole) sample of 7-(3-chloropropoxy)-2H-1-benzopyran-2-one as prepared in Example 1 above, 2 g (0.012 mole) 4-(2-thienyl)tetrahydropyridine, and 5 g NaHCo₃ in 80 ml DMF is stirred at 80°-90° C. for seven hours at room temperature overnight then filtered and evaporated in vacuo. The residue in methylene dichloride is washed with NaHCO₃, dried (MgSO₄) and evaporated in vacuo. 7-[3-[3,6-Dihydro-4-(2-thienyl)-1(2H)-pyridinyl]propoxy]-2H-1-benzopyran-2-one as 4.3 g of dark oil was obtained. The oil was dissolved in 20 ml of 2-propanol and treated with 3 ml of 20% 2-propanolic hydrogen chloride solution to give 2.4 g of the monhydrochloride salt, mp 235-7° C.

Anal. calcd. as: C₂₁H₂₁NO₃S.HCl.0.5H₂O. C, 60.99; H, 5.62; N, 3.39. Found: C, 61.06; H, 5.60; N, 3.27.

We claim:

1. A compound of the formula

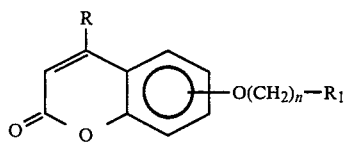

wherein n is an integer from 2–5; R is hydrogen, lower alkyl, trifluoromethyl, or lower alkoxy; R₁ is a radical of the formula

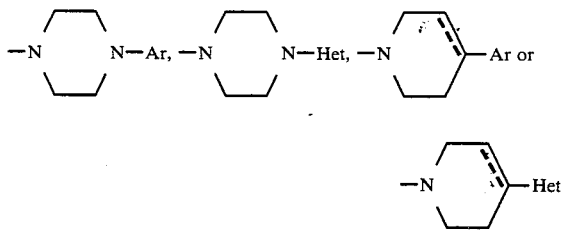

in which --- represents a single or double bond, Ar is phenyl or phenyl substituted by lower alkyl, lower alkoxy, lower thioalkoxy, halogen, or trifluoromethyl, and Het is 2-, 3-, or 4-pyridinyl or 2-, 3-, or 4-pyridinyl substituted by lower alkyl, lower alkoxy, or halogen; 2-, 4-, or 5-pyrimidinyl, or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl, or 2- or 3-thienyl substituted by lower alkyl or halogen; 2- or 3-furanyl, or 2- or 3-furanyl substituted by lower alkyl or halogen, or 2- or 5-thiazolyl or 2- or 5-thiazolyl substituted by lower alkyl or halogen, or a pharmaceutically acceptable acid addition salt thereof, with the exclusion of the compound wherein R is hydrogen or lower alkyl and R₁ is a radical of the formula

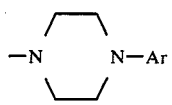

in which Ar is phenyl or phenyl substituted by lower alkyl, lowe alkoxy, halogen, lower thioalkoxy, or trifluoromethyl.

2. A compound according to claim 1 and of the formula

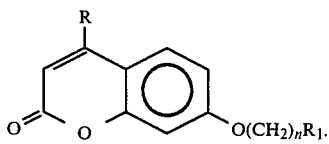

3. A compound according to claim 2, wherein R is hydrogen.

4. A compound according to claim 3, wherein R₁ is a radical of the formula

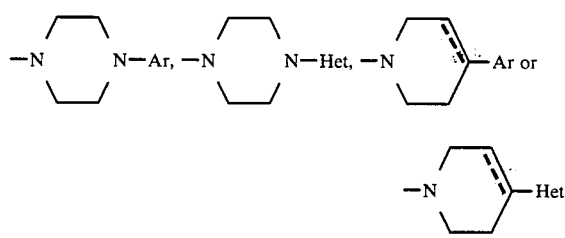

in which --- is a single or double-bond; Ar is phenyl or phenyl substituted by methyl, methoxy, thiomethoxy, or chloro, and Het is 2-, 3-, or 4-pyridinyl, 2-, 3-, or 4-pyridinyl substituted by methyl, chloro, or bromo; 2-, 4-, or 5-pyridimidinyl; 2-pyrazinyl, or 2- or 5-thiazolyl.

5. A compound according to claim 4, wherein R₁ is a radical of the formula

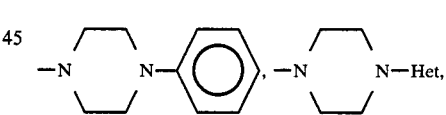

in which Het is 2-, 3-, or 4-pyridinyl; 2-, 4-, or 5-pyrimidinyl; 2-pyrazinyl, or 2- or 5-thiazolyl.

6. A compound according to claim 5, wherein n is 3 or 4.

7. A compound according to claim 6 and being 7-[3-[4-(2-pyrimidinyl)-1-piperazinyl]propoxy]-2H-1-benzopyran-2-one or a pharmaceutically acceptable acid addition salt thereof.

8. A compound according to claim 6 and being 7-[3-(1,2,4,6-tetrahydro-4-phenyl-1-pyridinyl)propoxy]-2H-1-benzopyran-2-one or a pharmaceutically acceptable acid addition salt thereof.

9. A compound according to claim 6 and being 7-[3-[3,6-dihydro-4-(2-thienyl)-1(2H)-pyridinyl]propoxy]-2H-1-benzopyran-2-one.

10. A method of treating psychosis in a subject suffering therefrom comprising administering to said subject an effective amount of a compound of the formula

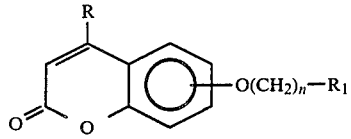

wherein n is an integer from 2–5; R is hydrogen, lower alkyl, lower alkoxy, or trifluoromethyl; $R_1$ is a radical of the formula

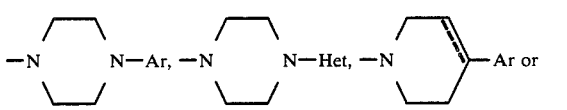

in which ═ is a single or double-bond; Ar is phenyl or phenyl substituted by lower alkyl, lower alkoxy, lower thioalkoxy, halogen, or trifluoromethyl, and Het is 2-, 3-, or 4-pyridinyl or 2-, 3 or 4-pyridinyl substituted by lower alkyl, lower alkoxy, or halogen; 2-, 4-, or 5-pyrimidinyl or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl or 2- or 3-thienyl substituted by lower alkyl or halogen; 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid salt thereof in unit dosage form.

11. The method of claim 10, wherein the compound is 7-[3-(4-phenyl-1-piperazinyl)propoxy]-4-methyl -2H-1-benzopyran-2-one or a pharmaceutically acceptable acid addition salt thereof in unit dosage form.

12. A method of treating anxiety in a subject suffering therefrom comprising administering to said subject an effective amount of a comound of the formula

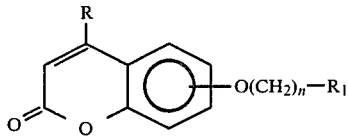

wherein n is an integer from 2–5; R is hydrogen, lower alkyl, lower alkoxy, or trifluoromethyl; $R_1$ is a radical of the formula

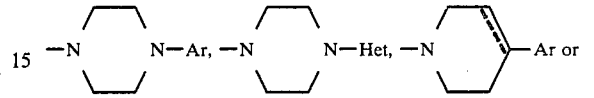

in which ═ represents a single or double bond, Ar is phenyl or phenyl substituted by lower alkyl, lower alkoxy, lower thioalkoxy, halogen, or trifluoromethyl, and Het is 2-, 3-, or 4-pyridinyl or 2-, 3-, or 4-pyridinyl substituted by lower alkyl, lower alkoxy, or halogen; 2-, 4-, or 5-pyrimidinyl, or 2-, 4-, or 5-pyrimidinyl substituted by lower alkyl, lower alkoxy, or halogen; 2-pyrazinyl or 2-pyrazinyl substituted by lower alkyl, lower alkoxy, or halogen; 2- or 3-thienyl, or 2- or 3thienyl substituted by lower alkyl or halogen, 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid salt thereof in unit dosage form.

13. A method of claim 12 wherein $R_1$ is a radical of the formula:

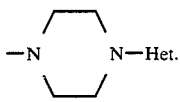

14. A method of claim 13 wherein $R_1$ is a radical of the formula:

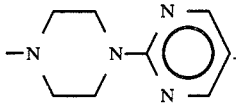

15. A method of claim 13 wherein the compound 7-[3-[4-(2-pyrimidinyl)-1-piperazinyl]propoxy]-2H-benzopyran-2-one.

16. A pharmaceutical composition comprising an antipsychotic or antianxiety effective amount of a compound of the formula of claim 1 with a pharmaceutically acceptable carrier.

* * * * *

UNITED STATES PATENT AND TRADEMARK OFFICE
CERTIFICATE OF CORRECTION

PATENT NO. : 4,701,456
DATED : October 20, 1987
INVENTOR(S) : Horace A. DeWald, et al.

It is certified that error appears in the above—identified patent and that said Letters Patent is hereby corrected as shown below:

In Column 14, Line 63, change "(1,2,4,6-tetrahydro-4-phenyl-1-pyridinyl]propoxy]-2H-" to --(1,2,3,6-tetrahydro-4-phenyl-1-pyridinyl]propoxy]-2H- --.

Signed and Sealed this

Fifth Day of April, 1988

*Attest:*

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,701,456

DATED : October 20, 1987

INVENTOR(S) : Horace A. Dewald, et al

It is certified that error appears in the above-identified patent and that said Letters Patent is hereby corrected as shown below:

Column 15, line 61, "comound" should read -- compound --.

Column 16, line 31, "3thie-" should read -- 3-thie --.

Signed and Sealed this

Second Day of August, 1988

Attest:

DONALD J. QUIGG

Attesting Officer

Commissioner of Patents and Trademarks